United States Patent
Biederman

(10) Patent No.: US 7,500,482 B2
(45) Date of Patent: Mar. 10, 2009

(54) CAPNOGRAPHY MEASUREMENT ADAPTER AND AIRWAY MASK SYSTEM

(76) Inventor: Paul D. Biederman, 11160 Oakenshield Cir., Columbia, MD (US) 21044

( * ) Notice: Subject to any disclaimer, the term of this patent is extended or adjusted under 35 U.S.C. 154(b) by 470 days.

(21) Appl. No.: 11/133,175

(22) Filed: May 20, 2005

(65) Prior Publication Data

US 2005/0257791 A1    Nov. 24, 2005

Related U.S. Application Data

(60) Provisional application No. 60/572,748, filed on May 21, 2004.

(51) Int. Cl.
*A61M 16/00* (2006.01)
(52) U.S. Cl. .................. 128/206.21; 600/532
(58) Field of Classification Search ............ 128/207.14, 128/200.26, 201.25, 207.18, 911, 912, 206.12, 128/206.21; 600/531, 532; 403/170, 174
See application file for complete search history.

(56) References Cited

U.S. PATENT DOCUMENTS

| | | | | |
|---|---|---|---|---|
| 2,705,954 A | * | 4/1955 | Andrews | 128/205.17 |
| 3,236,236 A | * | 2/1966 | Hudson | 128/207.17 |
| 3,721,236 A | * | 3/1973 | Bardehle | 128/201.11 |
| 5,101,834 A | * | 4/1992 | Wallace | 600/532 |
| 5,311,862 A | * | 5/1994 | Blasdell et al. | 128/205.25 |
| 5,937,858 A | | 8/1999 | Connell | |
| 6,098,617 A | | 8/2000 | Connell | |

* cited by examiner

*Primary Examiner*—Steven O Douglas
(74) *Attorney, Agent, or Firm*—Rosenberg, Klein & Lee

(57) ABSTRACT

A capnography measurement adapter and airway mask system includes a pair of gas input conduits for insertion into a nasal chamber of a mask housing. An adapter is mounted on the mask housing and includes a pair of suction conduit tubes for removal of air within the nasal housing. A sleeve member having a through passage extends into an internal chamber of the adapter and is fluidly coupled to a capnography monitor through a catheter and capnography monitor tubing.

15 Claims, 3 Drawing Sheets

CAPNOGRAPHY MEASUREMENT ADAPTER AND AIRWAY MASK SYSTEM

This Patent Application is based upon Provisional Patent Application 60/572,748 filed at the U.S. Patent and Trademark Office on 21 May 2004.

BACKGROUND OF THE INVENTION

In the medical and dentistry fields it is quite often necessary to sedate a patient. In particular in the field of dentistry where often times there are in-office sedations performed, a number of dental organizations and State Boards are defining and requiring monitoring of the carbon dioxide level of sedated patients through use of a number of medical devices such as pulse oximetry, pre-cordial stethoscope, blood pressure cuffs and capnography.

Capnography is the quantitative reading of carbon dioxide of a patient by means of infrared spectrometry. Expired air is drawn into a capnograph monitor through a vacuum pump located and positioned internal the capnograph monitor. The capnograph monitor then provides a continuous quantitative measurement of carbon dioxide levels during a particular procedure. When the source is a normal breathing patient there is a regular rhythmical rise and fall of the quantitative carbon dioxide data with each breath of the patient and a rhythmic wave is then recorded and displayed. The carbon dioxide level is read out on either a display monitor or a running graph paper readout. Use of a capnograph monitor also allows a healthcare provider to monitor the respiratory rate of the patient during the procedure.

The use of capnography is a distinct advantage to the healthcare provider, however, the use of capnography monitors has been limited in the past due to the fact that when performing capnography the connection for the device on the patient end requires either insertion into an endotracheal tube, or insertion or placement of a nasal cannula which is fixed on the face of the patient in near proximity to the exhaled breath, or in some cases puncturing a nasal hood or air mask and inserting a cannula into the nasal hood.

FIELD OF THE INVENTION

This invention relates to the medical and dental fields where a patient is undergoing a procedure where sedating or other gas is applied to the patient during a procedure.

In particular this invention pertains to measuring carbon dioxide levels of a patient undergoing a medical or dental procedure.

This invention further relates to the field of capnography measurement in the medical and dentistry fields.

In particular, this invention pertains to a combined capnography measurement adapter and airway mask system for permitting sedation of the patient while simultaneously monitoring carbon dioxide levels.

More in particular, this invention directs itself to a capnography measurement adapter and airway mask system where the capnography monitoring interface elements are mounted in fixed fashion to an adapter which is secured to and extends through an airway mask or nasal hood.

Still further, this invention directs itself to a system which permits the attending physician or dentist or health care provider to easily attach a suction catheter to a coupling member which in itself is coupled to a capnography monitor tubing.

Further, this invention pertains to a system where the attending physician or dentist or health care provider may easily attach an airway mask and further couple the airway mask and adapter to a capnography monitoring unit with a great efficiency of time and reliability.

PRIOR ART

When using capnographic techniques in combination with a sedation process, one prior art system allows for the insertion of the capnography monitor tubing into an endotracheal tube. However, in order to place an endotracheal tube requires the patient to be unconscious or paralyzed and such must be performed by highly trained medical personnel. Such use may cause discomfort to the patient and further increases the cost of the capnographic readings to be taken.

In some prior art systems, in order to obtain capnographic readings, it is necessary for insertion or placement of a nasal cannula which is taped or otherwise adhered to the face of the patient in close proximity to the exhaled breath. However, the nasal cannula often times is not well tolerated by a highly anxious patient who needs sedation and may interfere with the medical gas intake by physically requiring room in the nares. Additionally, the tubes of the nasal cannula may press against the face of the patient if the tubes are placed under a gas mask such as a nitrous-oxide mask.

In other prior art systems where the nasal cannula is taped to the face of the patient it has been found that additional time is required for the procedure and further the tube may be displaced during the procedure which is deleterious to the monitoring process.

In other prior art systems the nasal hood or air mask is punctured and the cannula is then inserted into the nasal hood. When a hole is punctured in the mask and a tube inserted through the punctured hole it is extremely difficult to fix the tube so that it does not become displaced. Taping time is consuming and the placement of the tubing is not accurate leading to possibly false carbon dioxide level readings.

Prior art techniques do not provide for a fast, reliable and practical methods to apply the capnograph to the patient.

Thus, there is a need in the field for a simple, cost effective, reliable and time optimal capnograph monitoring system when used in combination with a nasal hood or air mask.

SUMMARY OF THE INVENTION

A capnography measurement adapter and airway mask system is provided which includes an airway mask housing. The airway mask housing is adapted to encompass the nasal passages of a patient. The airway mask forms a nasal chamber and a pair of gas delivery tubes are secured to the airway mask housing which are in fluid communication with the nasal chamber for insert of a gas into the nasal chamber. A capnography adapter is mounted on the airway mask housing with the capnography adapter being coupled to a pair of gas exhaust tubes in fluid communication with the nasal chamber for removal of expired air from the patient. A capnography sleeve member is secured to a sidewall of the adapter with the sleeve member being in fluid communication with an interior of the capnography adapter at a proximal end thereof and insertable within a suction catheter at a distal end.

An object of the invention is to obtain an accurate readout of the carbon dioxide level of a patient during a medical or dental procedure.

A further object of the invention is to provide a system which minimizes the time duration of a medical or dental procedure by incorporating a capnography adapter into a nasal hood, or other airway device.

A still further object of the invention is to provide a capnography adapter which may easily and quickly be coupled to a capnography monitor to reduce the time of a procedure and resulting stress imposed on a patient.

A further object of the invention is to provide a combined gas flow system and a capnography monitor with all elements being secured to an air mask or nasal hood, or other airway device.

DESCRIPTION OF THE PREFERED EMBODIMENTS

Figure 1:
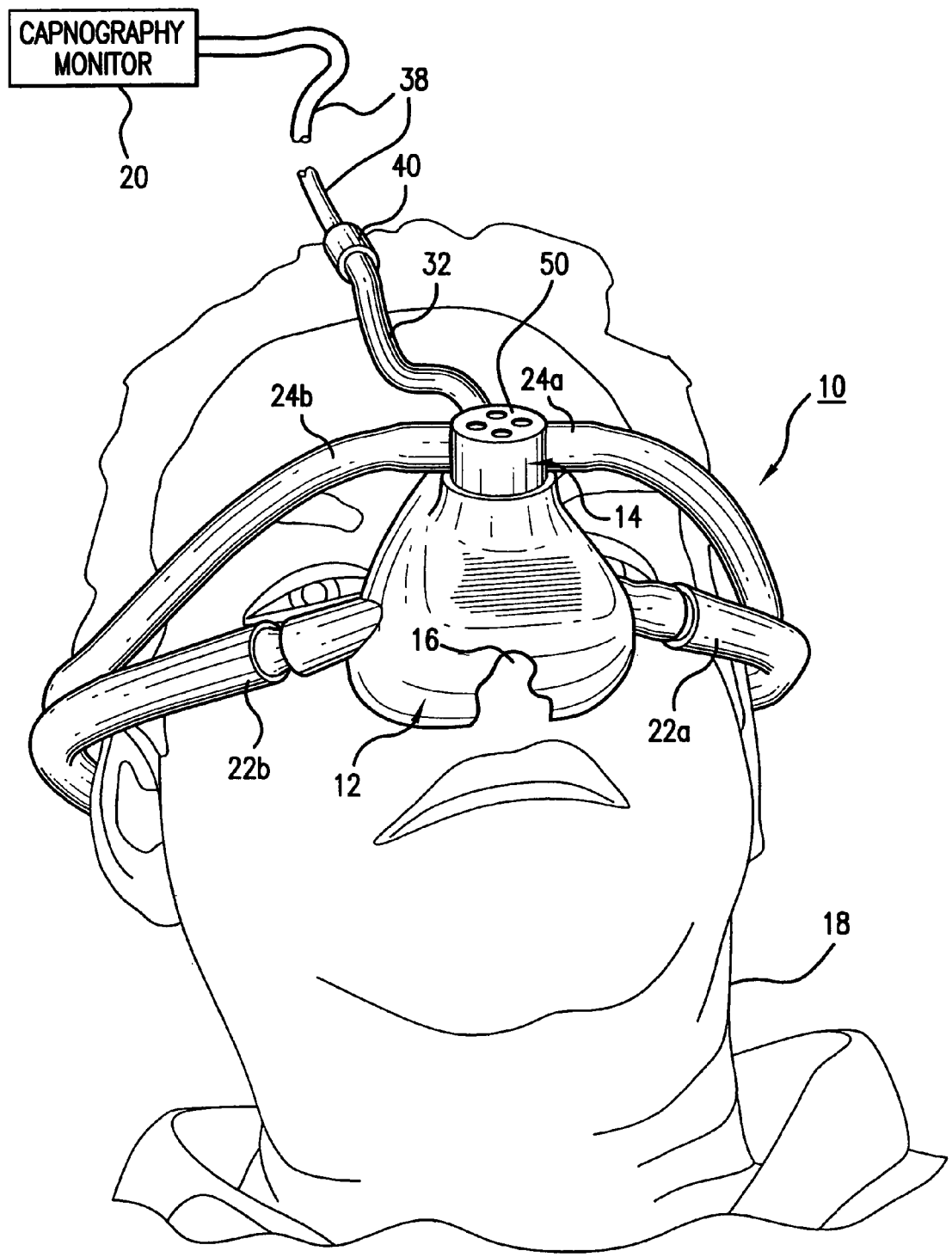
FIG. 1 is a schematic view of a patient having the capnography measurement adapter and airway mask system mounted over the patient's nasal passages.
Figure 2:
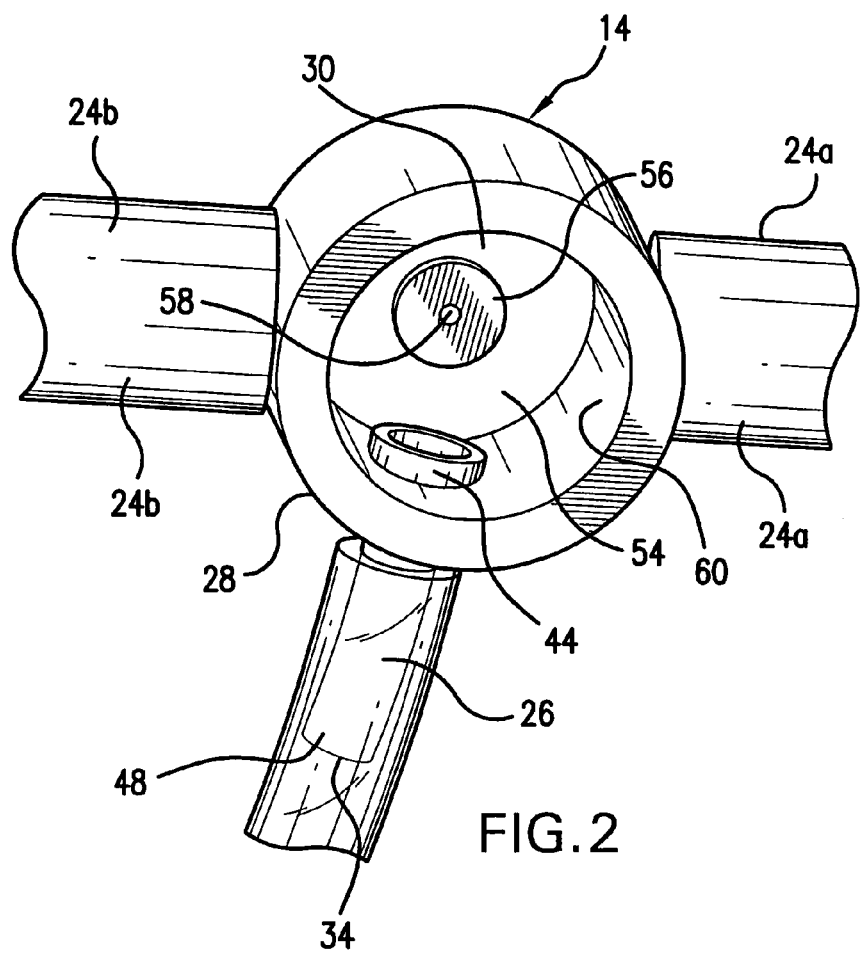
FIG. 2 is a perspective view partially cut away showing a lower section of the capnography adapter.
Figure 3:
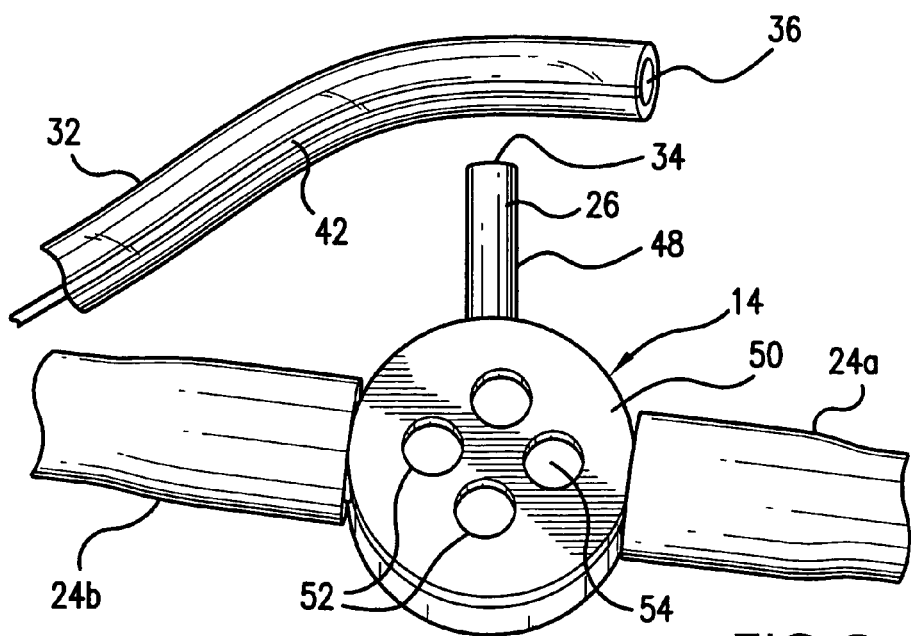
FIG. 3 is a top perspective view of the adapter showing a sleeve member mounted to the adapter for insert into a suction tube.

Referring now to FIGS. 1-3 there is shown a capnography measurement adapter and airway mask system 10 adapted to be placed over the nasal passages of patient 18 to aid in sedation of patient 18 during a dental procedure or other medical type of procedure. In particular, capnography measurement adapter and airway mask system 10 is particularly of use with capnography monitor 20 to aid in quantitative reading of carbon dioxide through means of infrared spectrometry. Capnograph monitors 20 are well known in the art and are commercially available. In the instant invention, a commercially available capnograph monitor manufactured by Critacare Systems, Inc. of Waukesha, Wis., model 8100 has been used. In general, capnograph monitor 20 includes a plastic through tube 38 which is coupled at one end to monitor 20 and at the other end to a source of carbon dioxide wherein the air is drawn into the capnograph monitor 20 through a vacuum pump internal to the capnograph. Capnograph through tube 38 is coupled to suction catheter 32 by standard coupler or ring 40. The capnograph monitor 20 provides for a continuous quantitative measurement of carbon dioxide generally displaying a rhythmical rise and fall in a normal breathing patient where the carbon dioxide level may be measured and displayed.

Figure 4:
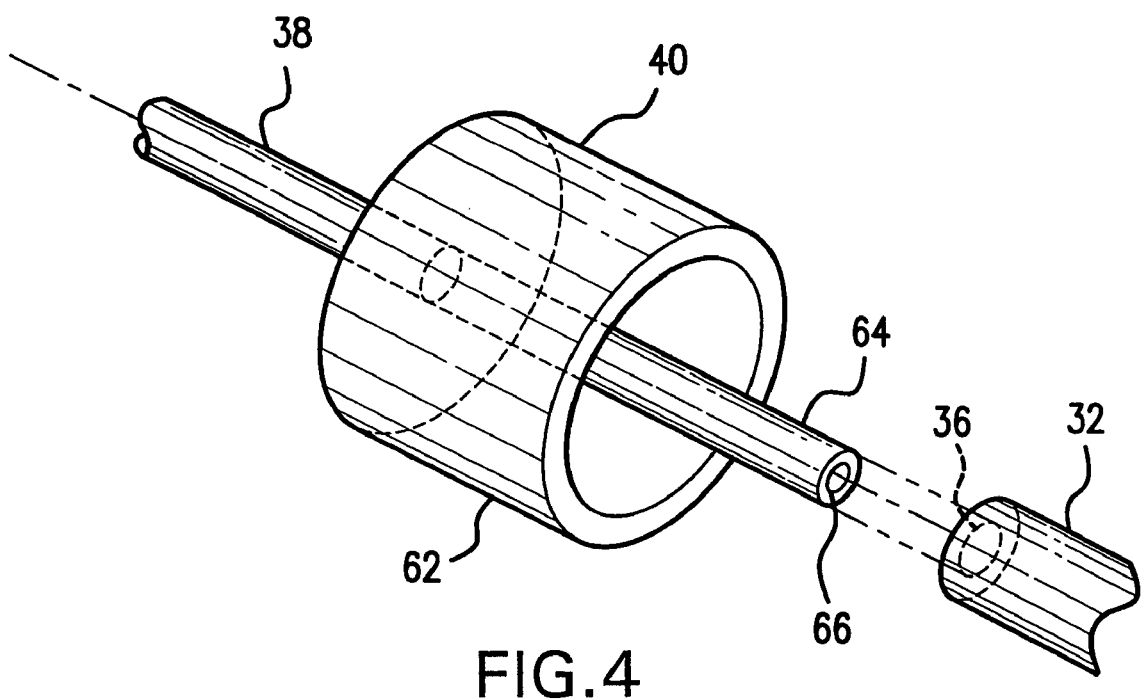
FIG. 4 is a schematic perspective, partially cut-away showing a coupler and a suction tube adapted for forming a fluid communication path to a capnography monitor.

As seen in FIG. 4, suction catheter 32 is adapted for insert into coupler 40. Coupler 40 is generally cylindrically contoured and includes coupler wall 62 having an internal lug extension 64 which is in fluid communication with capnograph monitor tubing 38. Lug extension 64 includes through opening 66 formed therethrough to provide a fluid path from suction catheter 32 through tubing 38 to capnography monitor 20.

Suction catheter 32 is formed to provide through opening 36 extending throughout the length of catheter 32. The external diameter of lug extension through opening 66 is substantially equal to the internal diameter of opening 36 to permit suction catheter 32 to be inserted over lug extension 64 in a removable manner.

In one example, lug extension member has an external diameter of approximately 4.0 mm with a corresponding dimension of the internal diameter of opening 36 of suction catheter 32 to permit a sliding fit upon insertion of catheter 32 onto lug extension 64.

Coupler 40 and components thereof such as lug 64 are generally formed of a closed cell plastic composition which allows easy insert of generally flexible suction catheter 32 thereon.

In this manner, the health care provider may easily and quickly attach suction catheter 32 to coupler 40 and create a fluid path from catheter 32 to capnograph monitor 40. This attachment scheme saves time in hooking monitor 20 to adapter 14 which may be critical during a procedure.

Capnography measurement adapter and airway mask system 10 as detailed in FIG. 1 includes airway mask housing or nasal hood 12 mounted over the nasal passages of Patient 18 and forming an internal nasal chamber 16. Airway mask may be one of a number of commercially available air masks commonly used in dentistry for in-office sedation as well as in the general medical field. Airway mask housing 12 is configured to permit a generally close interface and contiguous contact with the patient's skin around the nasal passages.

Adapter and airway mask system 10 further includes a pair of gas delivery tubes 22a, 22b shown in FIG. 1 which are secured to airway mask housing 12 and in fluid communication with the nasal chamber 16 for insert of a sedating or other type gas into the nasal chamber 16. Gas delivery tubes 22a and 22b are fluidly connected in standard fashion to a gas distribution device well known in the art and not forming part of the invention as herein described. Gas delivery tubes 22a/22b may be formed of the standard plastic composition which permits conforming and positioning of gas delivery tubes 22a, 22b in optimum positional location. The important criteria is that the sedating or other gas is insertable through airway mask housing 12 into nasal chamber 16 formed therein for inhalation by patient 18.

Capnography adapter 14 is mounted on airway mask housing 12 as is clearly seen in FIG. 1. Capnography adapter 14 is coupled and in fluid communication to a pair of gas exhaust tubes 24a, 24b for removal of expired air from patient 18. Gas exhaust tubes 24a, 24b are passed through a wall of capnography adapter 14 and are in fluid communication with nasal chamber 16 for removal of expired air from patient 18. Additionally, adapter 14 provides a mechanism whereby expired air from the patient 18 is directed to capnography monitor 20. Expired air is brought to capnography monitor through a pressure drop provided by a vacuum suction created by a vacuum mechanism within monitor 20.

Capnography sleeve member 26 shown in FIG. 2 is secured to a sidewall 28 of capnography adapter 14. Capnography sleeve member 26 is in fluid communication with an interior 30 of capnography adapter 14 at a proximal end thereof and is in itself insertable within suction catheter 32 at a distal end 34 shown in FIG. 3.

Capnography sleeve member 26 is force fitted to suction catheter 32 within through opening 36. Sleeve member 26 is formed of sleeved longitudinal extension member 48 and flange portion 44 as is seen in FIG. 2. Additionally, suction catheter 32 is in fluid communication with capnograph monitor 20 through capnograph monitor tubing 38 through standard coupling device 40 (previously described) which joins suction catheter 32 and capnograph monitor tubing 38. In this manner, there is fluid communication from capnography adapter 14 through a tube to capnograph monitor 20. The external diameter of capnography sleeve longitudinal extension member 48 is substantially equal to but slightly less than the internal diameter of suction catheter opening 36. In one commercial embodiment used the external diameter of sleeve longitudinal extension member 48 is 4 mm.

In general, capnography sleeve member 26 including the flange portion 44 and the sleeve longitudinal extension member 48 is formed of a metal composition such as brass; however, the particular composition is not of importance with the exception that it should be compositionally inert, rigid, stable and fixed for the purposes of interaction with the gases passing therethrough, When brass composition is used, the outer portion of the capnography member 26 is generally sand blasted. Epoxy cement is then applied to the surfaces of the flange portion 44 and permits the sleeve member to adhere to the inner surface 60 of adapter 14. Epoxy is placed on all sides of the sleeve member 26 which interface with sidewall 28 of adapter 14 and the excess epoxy is then cleaned therefrom. The epoxy sets for a predetermined time interval, usually 24 hours. In this manner, sleeve member is fixedly secured to adapter 14.

Suction catheter 32 shown in FIGS. 1-3 is generally formed of a plastic composition and includes a metallic wire 42 extending throughout the length suction catheter 32 which permits positional placement of suction catheter 32 in predetermined positional location. Wire 42 is flexible in nature which permits bending or other displacement of suction catheter 32 while simultaneously permitting suction catheter 32 to be positionally stable after the health care provider has optimally located suction catheter 32 with respect to patient 18. This is important in that it is generally desired to maintain suction catheter 32 in a displaced location from the face or skin of patient 18.

Capnography sleeve member 26 includes flange portion 44 previously described and seen in FIG. 2 which is secured to inner surface 60 of capnography adapter 14. Extending from flange 46 is the sleeve longitudinal extension member 48 which is then insertable within through opening 36 of suction catheter 32. Sleeve longitudinal extension member 48 is secured to flange member 44 in one piece formation or otherwise secured thereto and passes through adapter sidewall 28.

As previously discussed, sleeve longitudinal extension member 48 is then frictionally mounted within suction catheter 32 by force fitting at a distal end of extended sleeve member 42. With flange member 44 adhesively secured to inner wall 46 of adapter 14 a secure and compact system is provided for fluid communication between adapter 14 and capnography monitor 20.

Suction catheter 32 is fluidly coupled to capnography monitor 20. In particular, coupling 40 joins suction catheter 32 to capnography monitor tube 38 to provide fluid communication between capnography adapter 14 and capnography monitor 20.

Capnography adapter 14 as is seen, is generally substantially cylindrically contoured forming an interior chamber 30. Capnography adapter 14 may be formed of a plastic type composition well known in the medical art or may be formed of any composition which is generally inert to the gases passing therein.

Sidewalls 28 of adapter 14 are generally circular in cross-section and form circumferential sidewalls 28 with a top wall 50 being formed in conjunction with circumferential sidewalls 28 in generally one piece formation. As seen in FIGS. 1 and 3, capnography adapter 14 includes a plurality of vent openings 52 which are formed through top wall 50 of adapter 14. Vent openings 52 provide a safety configuration whereby air may be drawn internal the nasal chamber 16 in the event of clogging or other malfunction of tubes 22a, 22b.

Diaphragm 54 is located below an inner surface of top wall 50 and is formed of some type of flexible composition such as rubber, well known in the art. Diaphragm 54 is sandwiched between cap 56 and an inner surface of top wall 50 and is maintained in place by a securing member 58 such as a rivet or some like securement. Thus, diaphragm 54 is located adjacent an inner surface of top wall 50 of adapter 14 in a manner which allows flexible movement of diaphragm 54.

As shown in FIG. 2, sleeve member 26 and particularly flange 44 is positionally placed on sidewall 28 in a displaced location from diaphragm 54 in order to allow flexibility of diaphragm 54. The placement and location of flange 44 insures that there is no interference with movement of diaphragm 54 and provides a safety feature of system 10.

In operation, the health care provider places the nasal hood or mask 12 over the nasal passages of patient 18. Suction catheter 32 is then adjusted with respect to positional location and joined to coupling member 40 which is in itself coupled to tubing 38. In this manner, the monitor 20 is placed in an operational mode with only a minimum of effort and time consumed by the health care providers.

Although this invention has been described in connection with specific forms and embodiments thereof, it will be appreciated that various modifications other than those discussed above may be resorted to without departing from the spirit or scope of the invention. For example, functionally equivalent elements may be substituted for those specifically shown and described, and in the process method steps described, particular steps may be reversed or interposed, all without departing from the spirit or scope of the invention as defined in the appended Claims.

What is claimed is:

1. A capnography measurement adapter and airway mask system comprising:
  (a) an airway mask housing adapted to encompass nasal passages of a patient and forming a nasal chamber therein;
  (b) a pair of gas delivery tubes secured to said airway mask in fluid communication with said nasal chamber for insert of a gas into said nasal chamber; and
  (c) a capnography adapter mounted on said airway mask housing, said capnography adapter being coupled to a pair of gas exhaust tubes in fluid communication with said nasal chamber for removal of expired air from said patient and a capnography sleeve member fixedly attached to a sidewall of said adapter, said sleeve member being fixedly attached and in fluid communication with interior of said capnography adapter at a proximal end thereof and insertable within a suction catheter at a distal end.

2. The capnography measurement adapter and airway mask system as recited in claim 1 where said capnography sleeve member is adhesively secured to an inner wall of said capnography adapter.

3. The capnography measurement adapter and airway mask system as recited in claim 2 where a distal end of said suction catheter is coupled to a capnography tube.

4. The capnography measurement adapter and airway mask system as recited in claim 1 where said capnography sleeve member includes: (a) a flange member secured to said inner wall of said capnography adapter; and, (b) a sleeve longitudinal extension member secured to said flange member and passing through said adapter sidewall.

5. The capnography measurement adapter and airway mask system as recited in claim 1 wherein said sleeve longitudinal extension member is force fitted within said catheter at a distal end of said sleeve longitudinal extension member.

6. The capnography measurement adapter and airway mask system as recited in claim 4 where said flange member is adhesively secured to said inner wall of said capnography adapter.

7. The capnography measurement adapter and airway mask system as recited in claim 4 wherein said catheter is fluidly coupled to a capnography monitor at a distal end thereof to provide fluid communication between said capnography adapter and said capnography monitor.

8. The capnography measurement adapter and airway mask system as recited in claim 4 where said capnography adapter is formed of a plastic composition.

9. The capnography measurement adapter and airway mask system as recited in claim 4 wherein said capnography adapter is substantially cylindrically contoured forming an adapter chamber therein.

10. The capnography measurement adapter and airway mask system as recited in claim 9 where said capnography adapter includes a circumferential sidewall and a top wall formed in one piece formation.

11. The capnography measurement adapter and airway mask system as recited in claim 10 wherein said capnography measurement adapter includes a plurality of vent openings formed through said top wall of said capnography adapter.

12. The capnography measurement adapter and airway mask system as recited in claim 11 including a diaphragm located adjacent an inner surface of said top wall of said capnography adapter.

13. The capnography measurement adapter and airway mask as recited in claim 12 including a cap member secured to said top wall of said capnography adapter, said diaphragm being sandwiched between said cap member and said top wall inner surface.

14. The capnography measurement adapter and airway mask as recited in claim 2 wherein said sleeve member is formed of a rigid composition.

15. The capnography measurement adapter and airway mask as recited in claim 2 wherein said suction catheter includes a flexible wire formed in a wall of said suction catheter and extending throughout said suction catheter length to permit positioning of said suction catheter.

* * * * *